US008043215B2

(12) United States Patent
Zhang et al.

(10) Patent No.: US 8,043,215 B2
(45) Date of Patent: Oct. 25, 2011

(54) DRUG TITRATION UTILIZING AN IMPLANTABLE MEDICAL DEVICE

(75) Inventors: Yunlong Zhang, Mounds View, MN (US); Yi Zhang, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 287 days.

(21) Appl. No.: 11/834,792

(22) Filed: Aug. 7, 2007

(65) Prior Publication Data

US 2009/0043289 A1 Feb. 12, 2009

(51) Int. Cl.
*A61B 5/00* (2006.01)
(52) U.S. Cl. ...................... 600/301; 604/891.1
(58) Field of Classification Search ............... 604/891.1, 604/502–507; 600/301
See application file for complete search history.

(56) References Cited

U.S. PATENT DOCUMENTS

| 5,781,442 | A  | * | 7/1998 | Engleson et al. .............. 700/214 |
| 6,045,513 | A  |   | 4/2000 | Stone et al. |
| 6,080,106 | A  |   | 6/2000 | Lloyd et al. |
| 6,102,874 | A  |   | 8/2000 | Stone et al. |
| 6,190,324 | B1 |   | 2/2001 | Kieval et al. |
| 6,280,409 | B1 |   | 8/2001 | Stone et al. |
| 6,409,662 | B1 |   | 6/2002 | Lloyd et al. |
| 6,454,705 | B1 | * | 9/2002 | Cosentino et al. ............ 600/300 |
| 6,529,771 | B1 |   | 3/2003 | Kieval et al. |
| 6,852,737 | B2 |   | 2/2005 | Bonifacio et al. |
| 2003/0092975 | A1 | * | 5/2003 | Casscells et al. ............. 600/300 |
| 2004/0063719 | A1 | * | 4/2004 | Adams et al. ............. 514/252.17 |
| 2004/0122487 | A1 |   | 6/2004 | Hatlestad et al. |
| 2004/0132633 | A1 |   | 7/2004 | Carter et al. |
| 2004/0133081 | A1 | * | 7/2004 | Teller et al. .................. 600/300 |
| 2005/0119711 | A1 | * | 6/2005 | Cho et al. ......................... 607/42 |
| 2005/0137626 | A1 | * | 6/2005 | Pastore et al. ..................... 607/3 |
| 2005/0197585 | A1 | * | 9/2005 | Brockway et al. ............ 600/486 |
| 2006/0116593 | A1 |   | 6/2006 | Zhang et al. |
| 2006/0253162 | A1 | * | 11/2006 | Zhang et al. .................... 607/26 |

OTHER PUBLICATIONS

Basile, M.D., Jan N. et al., "Titration of Beta-Blockers in Heart Failure. How to Maximize Benefit While Minimizing Adverse Events", *Postgraduate Medicine Online* www.postgradmed.com Mar. 2003, pp. 1-10.

* cited by examiner

*Primary Examiner* — Patricia Mallari
*Assistant Examiner* — Michael D'Angelo
(74) *Attorney, Agent, or Firm* — Pauly, DeVries Smith & Deffner, L.L.C.

(57) ABSTRACT

A method for titrating a drug to provide a medical therapy to a patient. The method includes the steps of providing an implantable medical device having a controller, providing one or more implantable sensors configured to sense physical parameters of the patient and configured to transmit signals to the controller. The method further includes the step of receiving signals from the one or more sensors at the controller. The method additionally includes processing the received signals to determine at least two cardiopulmonary characteristics of the patient. The method also includes determining a composite index based on the at least two cardiopulmonary characteristics. In addition, the method includes generating a signal based on the composite index. Medical device systems are also disclosed.

29 Claims, 4 Drawing Sheets

DRUG TITRATION UTILIZING AN IMPLANTABLE MEDICAL DEVICE

FIELD OF THE INVENTION

The invention relates to the administration of drugs to patients where drug titration is required, and in some embodiments, to the titration of beta blockers for the treatment of heart disease.

BACKGROUND OF THE INVENTION

Congestive heart failure (CHF), also called just heart failure, is a condition that can result from any structural or functional cardiac disorder that impairs the ability of the heart to fill with blood or to pump a sufficient amount of blood throughout the body. Heart failure is a common syndrome. By one estimate, heart failure affects 5 million people in the U.S. and 550,000 new cases are diagnosed each year.

One characteristic of heart failure, among others, is autonomic imbalance. Continuously high sympathetic tone can cause increased heart rate, cardiac oxygen consumption, and risks of arrhythmias. Therefore, a common medical therapy for the treatment of heart failure is the administration of beta blockers. Examples of beta-blockers that are indicated for the treatment of heart failure include bisoprolol, carvedilol, and extended-release metoprolol. Beta blockers block the action of certain central nervous system neurotransmitters, such as epinephrine (adrenaline) and norepinephrine (noradrenaline), on the receptors of the sympathetic nervous system that mediate the "fight or flight" response. For example, stimulation of certain receptors by epinephrine induces a positive chronotropic and inotropic effect on the heart and increases cardiac conduction velocity and automaticity. Beta blockers also have an antiarrhythmic effect, which arises from the depression of sinus node function and atrioventricular node conduction, and prolonged atrial refractory periods. Beta blockers inhibit normal epinephrine-mediated sympathetic actions, but have minimal effect on resting patients. That is, they reduce the effect of excitement/physical exertion on heart rate and force of contraction, dilation of blood vessels, opening of bronchi, reduce tremor, and breakdown of glycogen.

However, the use of beta blockers can also result in side effects. The administration of beta blockers is a balance between the effectiveness of the drug in treating the heart disease or other medical condition and the side effects. Because beta blockers tend to depress cardiac activity, a primary side effect is bradycardia or low heart rate. In many cases, the ideal balance point is defined as the dosage of beta blockers that results in a desired resting heart rate, where further increases in dosage would result in a heart rate that is undesirably low. Other side effects of beta blockers include atrioventricular block, which is a delay or interruption in the conduction of electrical signals from the atria to the ventricles, resulting in arrhythmias or bradycardia. Furthermore, beta blockers may also cause hypotension, where the patient's blood pressure is too low, because of the depressive effects of the beta blockers on the patient's cardiac system. Certain other drugs, such as certain antiarrhythmics, can create similar side effects.

The balance between therapy and side effects generally requires that a patient undergoing drug therapy go through a drug titration procedure. Basically, drug titration normally involves first administering a relatively small dosage of a drug, then monitoring the patient's side effects, and subsequently increasing the dosage of the drug until the targeted benefits are achieved or until the patient's side effects meet or exceed a desired threshold. The dosage is increased until the patient's side effects increase to the point that they are judged to warrant no further increase in dosage or that the patient reaches a maximum recommended dosage.

However, improved techniques are needed for drug titration. Current techniques do not necessarily yield optimum results. Furthermore, current drug titration techniques require face-to-face interaction with medical personnel, which consumes resources and is inconvenient for the patient.

SUMMARY OF THE INVENTION

One aspect of the invention relates to a method for titrating a drug to provide a medical therapy to a patient. The method includes the steps of providing an implantable medical device having a controller and providing one or more implantable sensors that are configured to sense physical parameters of the patient and are also configured to transmit signals to the controller. The method further includes the step of receiving signals from the one or more sensors at the controller. Furthermore, the method includes the step of processing the received signals to determine at least two cardiopulmonary characteristics of the patient. In addition, the method includes the step of determining a composite index based on the at least two cardiopulmonary characteristics of the patient. Furthermore, the method includes generating a signal based on the composite index.

Another aspect of the invention relates to a medical device system for use with a drug titration protocol. The medical device system includes a controller and one or more implantable sensors configured to sense physical parameters of the patient and configured to transmit signals to the controller. The system is configured to receive signals from the one or more sensors and process the received signals to determine at least two cardiopulmonary characteristics of the patient, determine a composite index based on the at least two cardiopulmonary characteristics, and generate a signal based on the composite index.

Another aspect of the invention relates to a medical device system for use with a drug titration protocol. The medical device system includes a controller and a plurality of implantable sensors configured to sense physical parameters of the patient and configured to transmit signals to the controller. The plurality of implantable sensors include at least an electrocardiogram sensor that receives cardiac electrical signals, a blood pressure sensor, and an intra-thoracic impedance sensor. The controller is configured to receive signals from the plurality of sensors and process the received signals to determine associated physical characteristics of the patient. The determination of physical characteristics includes determining heart rate, mean arterial blood pressure, the presence and degree of atrio-ventricular block, pulmonary edema status, the presence and degree of dyspnea, and CSR/AHI burden. The controller is further configured to assign an index value to each physical characteristic based on its nature or degree, determine a composite index of physical characteristics by combining the individual index values, and generate a signal based on the composite index, where the signal provides an indication of the patient's tolerance of a beta-blocker or the effectiveness of a beta-blocker.

The invention may be more completely understood by considering the detailed description of various embodiments of the invention that follows in connection with the accompanying drawings.

Figure 1:
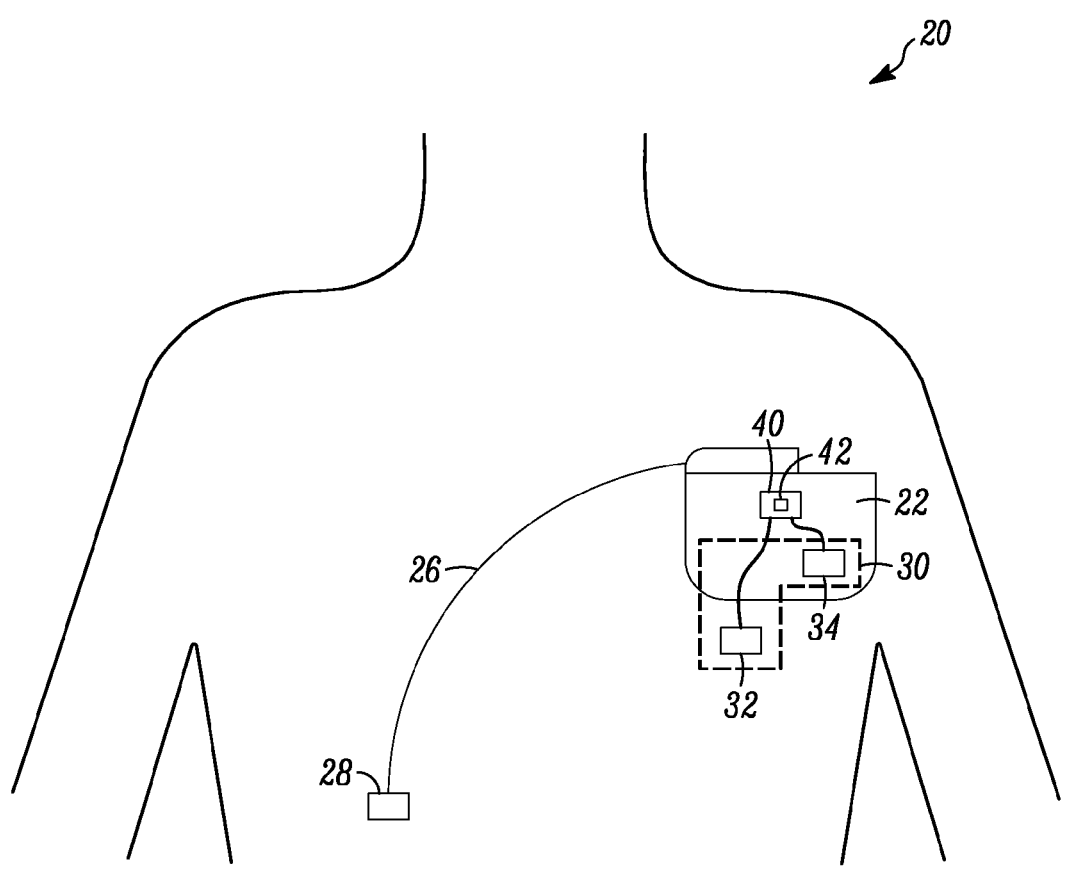
FIG. 1 is a schematic of a patient having an implantable medical device system for use with the present invention.

While the invention may be modified in many ways, specifics have been shown by way of example in the drawings and will be described in detail. It should be understood, however, that the intention is not to limit the invention to the particular embodiments described. On the contrary, the intention is to cover all modifications, equivalents, and alternatives following within the scope and spirit of the invention as defined by the claims.

DETAILED DESCRIPTION OF THE INVENTION

There is an overlap between the population of patients with heart failure and the population of patients with implantable medical devices, such as cardiac rhythm management devices (CRM). CRM devices include pacemakers, implantable cardioverter defibrillators (ICD), and cardiac resynchronization therapy (CRT) devices, among others. Many patients with heart failure already have a CRM device, and therefore techniques that use a CRM device to monitor the side effects and effectiveness of drugs used to treat heart failure will likely find significant application.

As mentioned above, beta-blockers are a key pharmacologic treatment option for patients with heart failure. However, the administration of beta-blockers and other similar types of drugs, such as antiarrhythmics, is a complex process because the proper dosages are difficult to determine. If the patient is not given a sufficient dosage, the drug may not adequately treat the patient's heart failure or other medical condition. If the patient is given too large of a dosage, the drug may create unpleasant and even serious side effects.

The inventors have devised a drug titration protocol that can be executed by or in conjunction with a patient's implantable medical device. This arrangement utilizes some of the capabilities inherent in a typical implantable medical device, and further incorporates additional sensors and telemetric communications to accomplish an appropriate drug titration protocol. The drug titration protocol has the advantage that it can be conducted with only minimal patient involvement and does not require a visit to a medical facility. This results in less inconvenience to the patient and less expense for the medical system. The protocol increases accuracy compared to conventional techniques because the patient's side effects can be more frequently monitored than when monitoring is only accomplished when the patient is seen in person by a medical professional.

An embodiment of drug titration system having an implantable medical device is depicted in FIG. 1. The drug titration system 20 includes an implantable medical device 22 such as a cardiac rhythm management (CRM) device. A CRM device may be, for example, a pacemaker, an implantable cardioverter defibrillator, or a cardiac resynchronization therapy (CRT) device. Other types of implantable medical devices are usable, however. In one embodiment, an implantable medical device (IMD) 22 has one lead 26 that forms an electrically conductive path to an electrode 28. Electrode 28 is in contact with cardiac tissue and is capable of sensing cardiac electrical activity. In another usable embodiment, IMD 22 does not have a lead, but rather uses subcutaneous cardiac electrical sensing to detect a patient's cardiac electrical activity. A cardiac electrical signal is transmitted from cardiac tissue to electrode 28 and through lead 26 to IMD 22, where it is received and forms the basis of an electrocardiogram that is indicative of the operation of the patient's heart. In addition, the implantable medical device 22 includes a controller 40. In some embodiments, controller 40 is capable of monitoring the cardiac electrical signals received from electrode 28 and lead 26, and determining a heart rate and other electrocardiogram intervals such as R-R interval and QT interval from the cardiac electrical signals.

Figure 4:
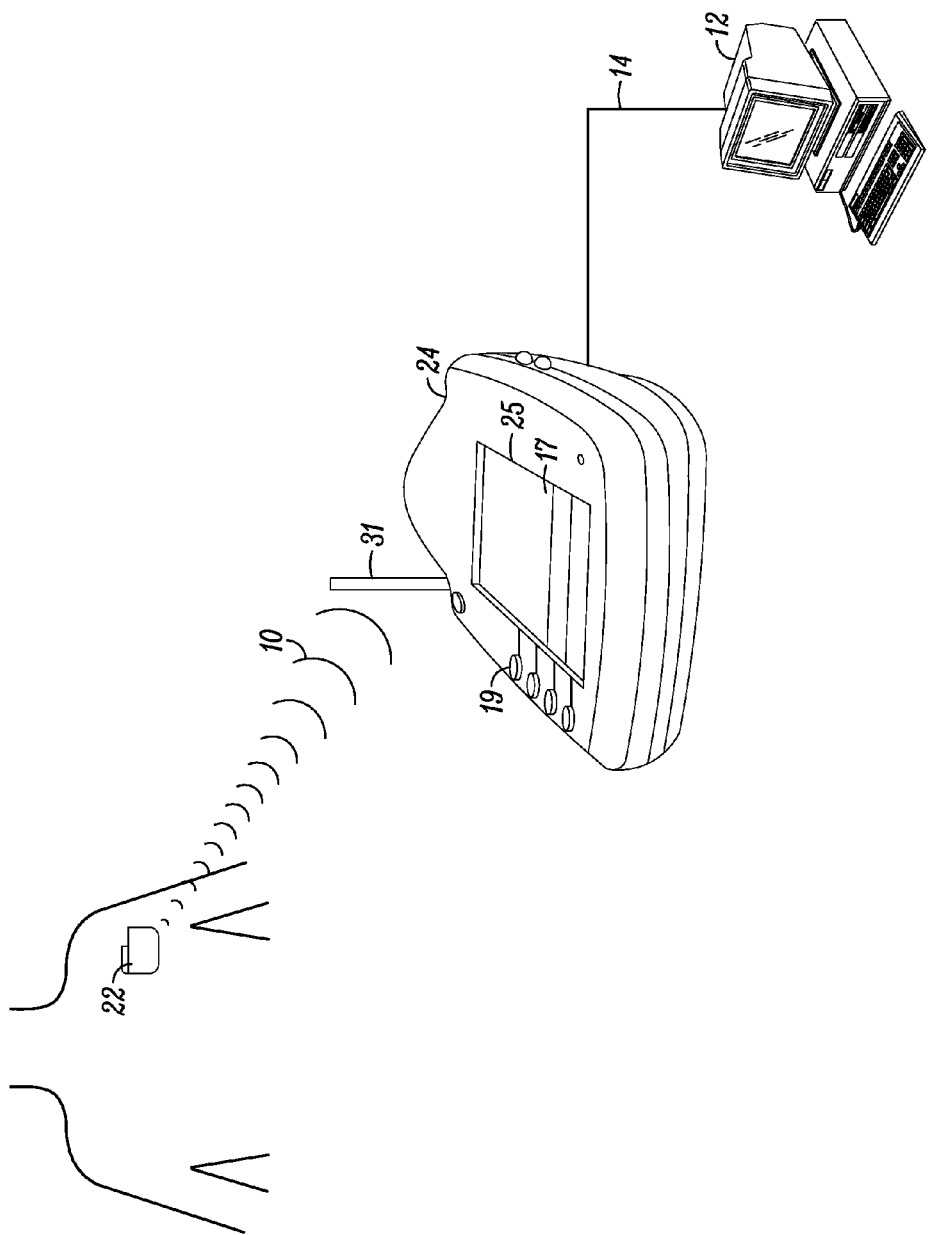
FIG. 4 is a schematic representation of a communication pathway from an implantable medical device to a patient interface device to a remote computer.

IMD 22 is further configured to communicate by telemetry with appropriately configured devices outside of the patient's body. For example, FIG. 4 illustrates a communication by telemetry from IMD 22 to a patient interface device 24. Exemplary patient interface devices 24 include, but are not limited to, the LATITUDE® patient management system, the Model 2920 Programmer, and the Model 3120 Programmer, each available from Boston Scientific Corporation, Natick, Mass. Patient interface device 24 includes an interface 25 that is capable of displaying information and/or messages that can be perceived and understood by a patient. In the embodiment of FIG. 4, the interface 25 includes a screen 17 for displaying information. Patient interface device 24 is also capable of receiving input from a patient. In the embodiment of FIG. 4, patient interface device 24 includes buttons 19 and touch sensitive screen 17 for receiving input. Patient interface device 24 further includes communication capabilities. Generally, patient interface device 24 is capable of communicating with implantable medical device 22 by telemetry, such as by wireless communication path 10. Patient interface device 24 includes antenna 31 configured for receiving and transmitting telemetric communications. In some embodiments, a patient interface device 24 includes a controller that is configured to receive and process signals.

Patient interface device 24 may also be capable of communicating with a remote computer 12 (also called a remote station 12) or through telecommunications, such as over a conventional phone line 14, through cellular phone communications, or any other wired or wireless form of communication. In some embodiments, patient interface device 24 is configured to inquire regularly about the patient's general health conditions, such as physical activity and symptoms of disease. Inquiring about the patient's health may involve displaying one or more health-related questions on an interface such as screen 17 and requesting the patient provide input such as through a touch sensitive screen 17 or buttons 19. The patient interface device 24 may also be configured to receive information from the implanted medical device 22 such as whether the patient's side effects and the drug's effectiveness are in a range where increasing the dosage of a drug is recommended or not recommended, and other information such as the operation of the device and any other information or data stored in the device. The patient interface device 24 may be further configured to transmit this information to a remote computer 12, where the information is received and can be further analyzed to determine the patient's medical condition. For example, the information may be transmitted from remote computer 12 to a physician who can use the information to determine whether to adjust the patient's dosage of a drug. The physician may also receive reminders in this way to maintain a preset drug titration schedule.

Drug titration system 20 of FIG. 1 further includes a plurality of implantable sensors 30. These sensors measure parameters related both to the beneficial effects of the drug being administered, as well as the side effects or non-beneficial effects. In some embodiments, an implantable sensor 30 has a wired connection to controller 40, and in other embodiments, an implantable sensor 30 transmits a wireless signal that is received by controller 40. In one embodiment, one of the implantable sensors 30 is an arterial blood pressure sensor 32 that is configured to sense the patient's blood pressure. In another embodiment, one of the implantable sensors 30 is a respiration sensor 34. A respiration sensor 34 may consist of an intra-thoracic impedance sensor that measures the impedance in the patient's chest area and determines respiration characteristics, or alternatively, the respiration sensor 34 may be a minute ventilation sensor that measures tidal volume and respiration frequency. Other respiration sensors are usable.

In some embodiments, the drug titration system 20 will include non-implantable sensors. For example, a non-implantable blood pressure sensor may be used in place of an implantable blood pressure sensor 32. An example embodiment of a non-implantable blood pressure sensor is a blood pressure cuff that the patient applies to his or her bicep to take blood pressure readings. Typically, a non-implantable sensor will be configured to transmit a signal through telepathy to the implantable device or via a wired or wireless signal to a patient interface device 24. A transmission from a non-implantable sensor to an implantable device may either be directly from the sensor to the implantable device, or may be from the sensor to another device such as a patient interface device that in turn transmits a signal to the implantable device.

Figure 2:
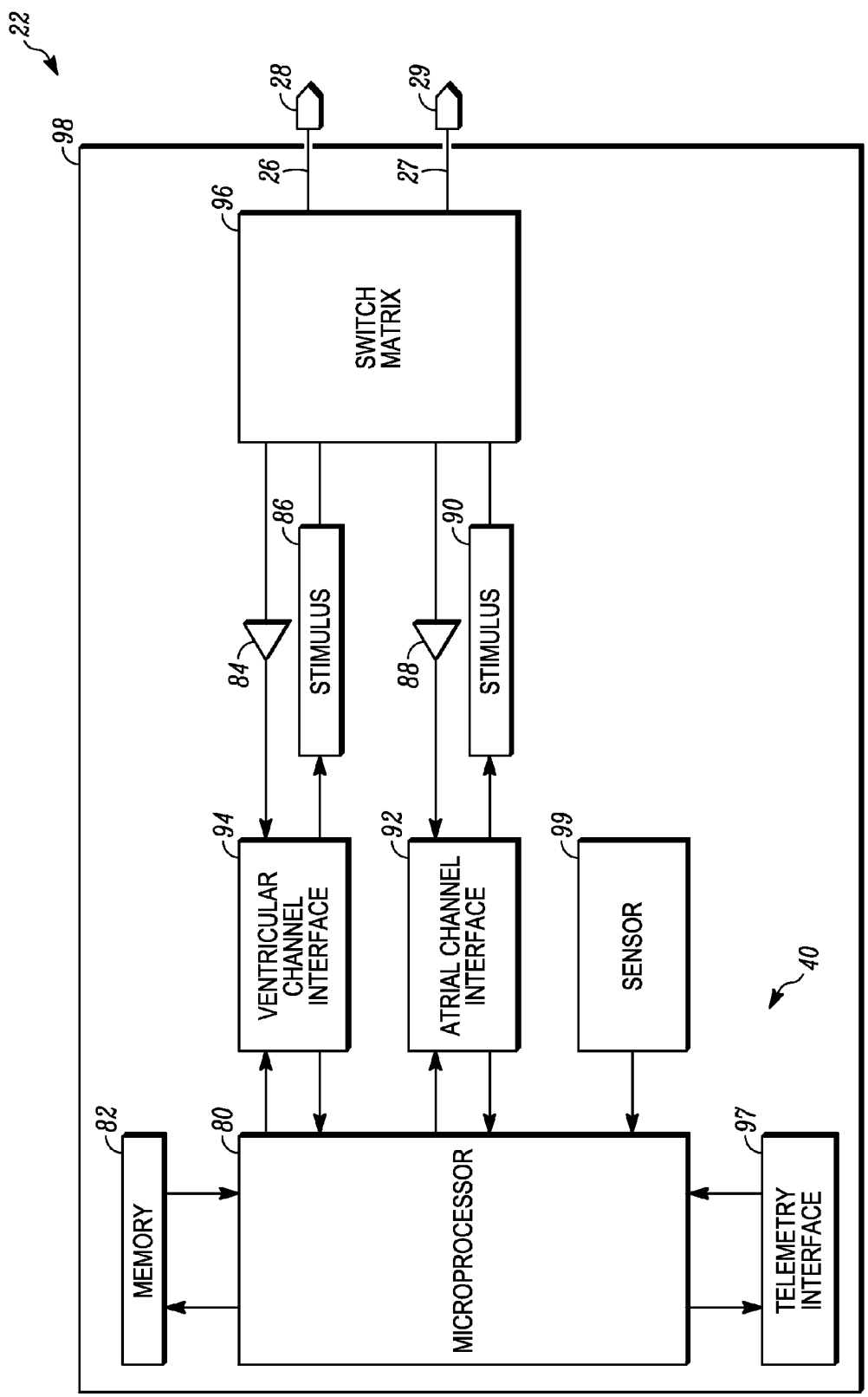
FIG. 2 is a schematic representation of functional elements of an embodiment of an implantable medical device.

FIG. 2 is a schematic depiction of the functional elements of one embodiment of a CRM device. Implantable medical device 22 is shown having lead 26 that forms an electrically conductive path to electrode 28. Electrode 28 is in contact with cardiac tissue and is capable of sensing cardiac electrical activity. A cardiac electrical signal is transmitted from electrode 28 through lead 26 to IMD 22, where it is received and forms the basis of an electrocardiogram that is indicative of the operation of the patient's heart. Some embodiments of a CRM device have two leads and two electrodes, such as second lead 27 and second electrode 29. As shown in FIG. 2, an IMD 22 may be further configured to communicate by telemetry with appropriately configured devices outside of the patient's body.

A controller 40 of IMD 22 senses cardiac events through a sensing channel and outputs pacing pulses to the heart via a pacing channel in accordance with a programmed pacing mode. A microprocessor 80 serves as the controller in the embodiment of FIG. 2 and communicates with a memory 82 via a bidirectional data bus. The memory 82 typically comprises a read-only memory (ROM) or random-access memory (RAM) for program storage and a RAM for data storage. The implantable medical device is shown in FIG. 2 as having two leads, each having a tip electrode. Alternatively, bipolar leads are provided with ring and tip electrodes.

The implantable medical device of FIG. 2 has atrial sensing and pacing channels comprising electrode 29, lead 27, sensing amplifier 88, output circuit 90, and an atrial channel interface 92 which communicates bidirectionally with a port of microprocessor 80. In this embodiment, the device also has ventricular sensing and pacing channels comprising electrodes 28, lead 26, sensing amplifier 84, output circuit 86, and ventricular channel interface 94. For each channel, the same lead and electrode can be used for both sensing and pacing. A switch matrix 96 may configure a channel for unipolar sensing or pacing by referencing an electrode of a unipolar or bipolar lead with the implantable medical device housing or can 98. The channel interfaces 92 and 94 include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers. The implantable medical device can also include one or more sensors 99, such as implantable sensors 30, which may include blood pressure sensor 32 and respiration sensor 34. A telemetry interface 97 is also provided for communicating with a non-implanted device, such as through an antenna 31.

Controller 40 of implantable device 22 receives signals from the various sensors 99 that are present, such as implantable sensors 30, as well as the cardiac electrical signals received from electrode 28. Controller 40 further includes memory 42 for storing one or more parameters associated with the operation of implantable device 22. These parameters may be permanently stored in memory 42, or may be programmable values that may be modified through a telemetric communication with an appropriately configured non-implantable device. For example, a physician may use a programming device having a wand that is placed over the patient's chest and that establishes a communication link with the implantable device 22 to upload a parameter to memory 42. Similarly, a physician or other trained medical person can transmit information or instructions to be stored in memory 42.

Figure 3:
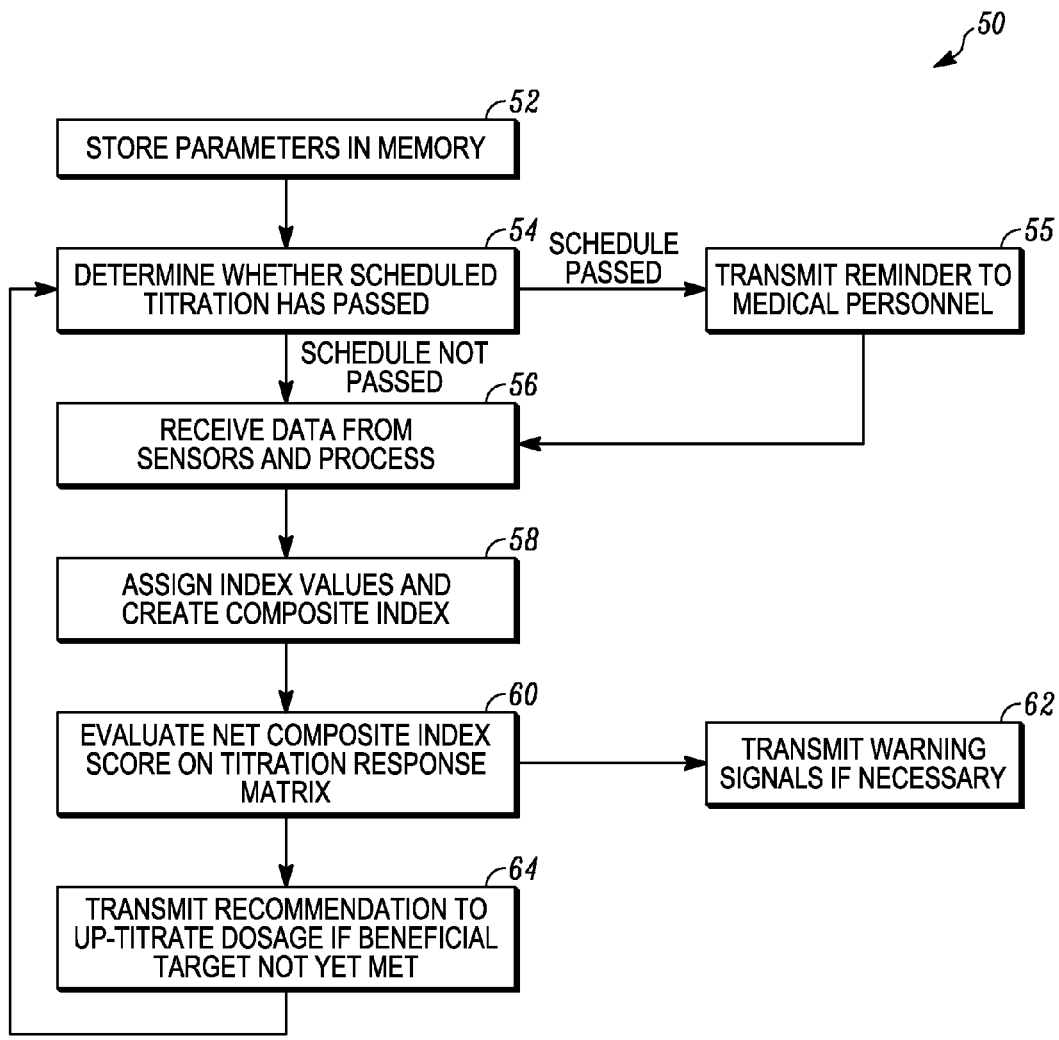
FIG. 3 is a flow chart of a titration technique according to the principles of the present invention.

A flow chart depicting an embodiment of an algorithm 50 for use with the present invention is shown in FIG. 3. In the embodiment of FIG. 3, step 52 of algorithm 50 includes storing parameters and any other needed operating information in memory 42. For example, in one embodiment the following parameters may be stored in memory 42:

(1) Starting drug dosage. This is a relatively small dosage that will be the starting dosage for a drug titration procedure, where the starting dosage is generally determined to have an extremely low risk of causing excessive side effects in a patient.

(2) Maximum drug dosage. This is the dosage that is the maximum a patient should ever receive, even if the drug-induced side effects do not constitute a limiting factor. This value is generally based on the recommendations of the drug's manufacturer, a consensus of medical professionals, and/or the judgment of a physician.

(3) Current or actual drug dosage. This is the dosage level that is currently being administered to the patient.

(4) Target resting heart rate. Because beta blockers and other similar drugs tend to reduce a patient's resting heart rate, this parameter is used to prevent dosages that would lower the patient's heart rate below a desired level. Generally, if the patient's resting heart rate is less than the target resting heart rate, then further increases in dosage will be avoided. In one embodiment, the target resting heart rate is 60 beats per minute.

(5) Titration interval. This is the amount of time between changes in dosage. The purpose of this parameter is largely to be able to transmit a message to a physician if the desired titration interval has been exceeded in order to encourage the physician to conduct the titration in a timely fashion. When the change in dosages has been done, or if the physician has elected to keep the dosage the same, an input is provided to reset a time counter. In various embodiments, the titration interval is one week, and in other embodiments, the titration interval is two weeks, and in further embodiments, other time periods are also usable.

(6) Side effect thresholds. These are parameters associated with the measurements of side effects that define the severity of the side effect. For each measurement or calculated quantity from the one or more sensors that measure the patient's physical condition, the side effect thresholds are used to define a score that represents the severity of each side effect.

(7) Composite index threshold. This value or values defines the recommended degree of oversight of the patient and/or the recommended change in the drug titration procedure based on the degree of the patient's side effects. The composite index can be determined through a number of techniques, and is a value that is reflective of the extent or degree of multiple physical characteristics of the patient. This parameter is discussed in more detail below.

Step 54 of algorithm 50 determines whether the scheduled titration period has passed. As shown in FIG. 3, if the tentative titration schedule has been exceeded, a reminder is generated at step 55 that is or can be transmitted to a physician or other medical person. This reminder may help the physician or other medical person to maintain a pre-determined titration schedule. In some embodiments, this step can be selectively turned on or off, and in other embodiments, this step is omitted. In some embodiments, after a reminder is transmitted at step 55, the algorithm 50 continues to step 56. In some embodiments, the transmission of the reminder will repeat at regular intervals until it is acknowledged by the medical personnel.

Step 56 of algorithm 50 involves receiving data from the various sensors and processing the raw sensor data to determine relevant physical characteristics. In some embodiments, the physical characteristics that are determined are cardiopulmonary characteristics or include cardiopulmonary characteristics. In some embodiments, at least two cardiopulmonary characteristics are determined. Generally, a cardiopulmonary characteristic means any characteristic relating to the cardiovascular or pulmonary system of a patient. Cardiopulmonary characteristics may include, for example, characteristics of the heart, vasculature, lungs, or blood. Cardiopulmonary characteristics may include aspects of blood composition, such as glucose, electrolytes, blood oxygen, etc. Cardiopulmonary characteristics generally do not include characteristics that are not directly indicative of cardiovascular or pulmonary systems, such as posture, physical activity level, etc. In some embodiments, processing sensor data is done in the controller of the IMD, and in other embodiments, processing is done outside of the patient's body, such as a patient interface device. Where processing is done by a device outside of a patient's body, the IMD is generally configured to transmit the sensor data to the external device.

As discussed above, the sensors used to determine the physical and/or cardiopulmonary characteristics may include a heart electrocardiogram sensor, blood pressure sensor, respiration sensor, etc. The processing required will vary based on the sensors present and the desired analysis. One typical processing step includes analyzing an electrocardiogram signal to determine the patient's heart rate, such as by measuring the R-R interval. In some embodiments, however, the usage of this parameter can be disabled, such as if the patient is in atrial fibrillation. In an embodiment where the heart rate parameter is disabled, the heart rate is not determined, a composite index score is not assigned for the heart rate parameter, and the scoring matrix is adjusted accordingly to compensate for the disabled parameter (the composite index and scoring matrix are discussed below). In other embodiments, a CRM device may be configured to pace the heart at a lower rate limit (LRL) that prevents the patient's heart rate from falling too low, and where the patient's heart rate is being controlled by the CRM device, then the step of determining the patient's heart rate may involve receiving a parameter from within the CRM device that is indicative of the pacing rate.

Further, the electrocardiogram may be analyzed to determine whether the patient has an arrhythmia, such as first degree, second degree, or third degree atrioventricular block (A-V block). First degree atrioventricular block is generally due to conduction delay in the atrioventricular node, and is determined by the presence of a P-R interval on the electrocardiogram of more than about 200 ms. Second degree atrioventricular block is generally considered to be either type 1 (also called Mobitz I) or type 2 (also called Mobitz II). Type 1 second degree atrioventricular block is generally caused by inhibited conduction through the atrioventricular node and is determined by the presence of a progressive increase in the P-R interval on consecutive beats of an electrocardiogram, followed by a dropped QRS complex, subsequently followed by a reset P-R interval. Type 2 second degree atrioventricular block is generally caused by inhibited conduction in the His-Purkinje System. It is identified by the QRS complex being intermittently nonconducted, where this is not preceded by progressive P-R prolongation and is not followed by P-R shortening. Third degree heart block is a condition where the impulses generated in the atria are not transmitted to the ventricles, and where the ventricles beat according to the autorhythmicity of the cells. Third degree heart block is characterized by significant beat to beat variability in the P-R interval, the result of there being no correlation between the P waves and the QRS complexes. In one embodiment, the patient is evaluated for A-V block once a day for 30 consecutive heart beats by temporarily changing the device pacing mode. In another embodiment, the patient is evaluated for other bradycardia arrhythmias and/or tachycardia arrhythmias.

Another processing step may be the analysis of a blood pressure sensor to determine the patient's blood pressure. A wide variety of blood pressure sensors are known to those of skill in the art and usable here, including implanted blood pressure sensors such as intra-arterial sensors or extra-arterial sensors, and non-implanted blood pressure sensors, such as blood pressure cuffs. Generally, the analysis of a blood pressure sensor involves determining the patient's mean arterial pressure (MAP), which is the average blood pressure over a single cardiac cycle. A further processing step is to determine the patient's pulmonary edema status if there is an intra-thoracic impedance sensor present. An intra-thoracic total impedance (ITTI) can be determined based on the impedance measurement in the patient's chest, where the ITTI is representative of the amount of fluid in the patient's lungs compared to the amount of air in the patient's lungs. This determination is made through the relationship that the impedance decreases as the amount of fluid increases. In one embodiment, the pulmonary edema status can be characterized by a percentage of fluid.

Yet another processing step involves determining the presence and degree of dyspnea in the patient. This is done by determining the patient's respiration rate, in breaths per minute, from the respiration sensor. Furthermore, the controller determines a Cheyne-Stokes Respiration (CSR) Burden and Apnea and Hypopnea Index to monitor for abnormal respiration patterns. Generally, the respiration sensor can determine the interval between breaths and the volume of each breath. In some embodiments, the patient's minute ventilation, respiration rate, as well as indications of ventricular tachycardia are evaluated to determine the presence of abnormal respiration patterns. The variability in the time interval or volume from one breath to the next is an indication of an abnormal respiration pattern. The percentage of abnormal respiration events can be used as an index of Cheyne-Stokes Respiration (CSR) Burden and Apnea and Hypopnea Index (AHI).

After receiving sensor data at step 56 and processing as described above, a composite index is created at step 58. One way of creating a composite index is by first assigning a score to the reading from each sensor, or alternatively, from the processed characteristic indicated by each sensor. Each individual score can be called an index value. These index values can then be combined to form a composite index. Another way of creating a composite index is by developing a logical structure, such as a logic tree, that utilizes the sensor readings and/or the processed characteristics to make a decision as to the appropriate composite index without first assigning individual index values. Other ways of creating a composite index are also usable. The composite index will then be a single value that represents the extent or severity of multiple physical characteristics of the patient.

In an embodiment where a composite index is created by assigning a score to the sensor readings or processed characteristics, a scoring matrix will typically be used to assign a score to the output received from each sensor, where the scoring matrix defines the index value that will be assigned to a particular measured or processed characteristic. Generally, each index value will be associated with a range or threshold of a measured or processed side effect or characteristic. Typically, there is one score or index value assigned and stored for the reading from each sensor. An example embodiment of a scoring matrix is depicted below:

|  | Index value | | | |
| --- | --- | --- | --- | --- |
|  | 0 | 1 | 2 | 3 |
| Bradycardia (heart rate, beats/min) | >=60 | 59-55 | 54-50 | <50 |
| A-V Block Degree | None/I AVB | II AVB (I) | II AVB (II) | III AVB |
| Hypotension (mean arterial pressure, mmHg) | >=70 | 69-65 | 64-60 | <60 |
| Pulmonary Edema (PE) status (ITTI) | ↑/— | ↓<=10% | ↓11-20% | ↓>20% |
| Dysnpnea (respiration rate, breaths/min) | <=20 | 21-25 | 26-30 | >30 |
| CSR/AHI burden | No change | ↑<=10% | ↑10-20% | ↑>20% |

The table above is only an example, and there are many different scoring matrices that are usable, where a scoring matrix may be constructed based on the judgment or desires of the patient's medical care team or other medical personnel. Furthermore, various embodiments of the invention may have various combinations of sensors, and the scoring matrix will be constructed to correspond to the sensors that are present. As seen in the example table above, the processed data from each sensor is assigned a score based on the indicated severity of the side effect. For example, a heart rate of greater than or equal to 60 beats per minute (bpm) is assigned a score of 0, a heart rate of 55-59 bpm is assigned a score of 1, a heart rate of 50-54 bpm is assigned a score of 3, and a heart rate of less than 50 bpm is assigned a score of 3. In some embodiments, such as where a CRM device paces at a lower rate limit of 60 beats or greater, such that the patient's heart will not beat at less than this lower rate limit, the fact that the CRM device is pacing the patient's heart may be used to assign a separate score not based on the scoring matrix. In one embodiment, if the CRM device is pacing the patient's heart, a score of 1 is applied for heart rate.

Likewise, if the patient's electrocardiogram does not exhibit atrioventricular block or first degree atrioventricular block, then an A-V block score is assigned to 0. Similarly, if the sensors indicate type 1 second degree atrioventricular block, then an A-V block score of 1 is assigned, and if type 2 second degree atrioventricular block is detected, then an A-V block score of 2 is assigned. Furthermore, if third degree atrioventricular block is detected, then an A-V block score of 3 is assigned.

As shown in the table above, if the patient's mean arterial pressure (MAP) is greater than or equal to 70 mmHg, then the blood pressure score is assigned to 0. However, MAP of 65-69 mmHg is assigned a score of 1, MAP of 60-64 mmHg is assigned a score of 2, and MAP of greater than 60 mmHg is assigned a score of 3. Furthermore, the patient's pulmonary edema status is assigned a score of 0 if the ITTI is increasing or zero, a score of 1 if the ITTI is decreasing and less than or equal to 10 percent, a score of 2 if the ITTI is decreasing and 11 to 20 percent, and a score of 3 if the ITTI is decreasing and greater than 20 percent.

In addition, the patient is assigned a dyspnea score based on the patient's measured respiration rate, where a score of 0 is associated with a respiration rate of less than or equal to 20 breaths per minute (br/min), a score of 1 is assigned for 21-25 br/min, a score of 2 for 26-30 br/min, and a score of 3 for greater than 30 br/min. The patient is also assigned a CSR/AHI burden score, where 0 is assigned where there is no change or decreasing, 1 is assigned if the CSR/AHI burden is increasing and less than or equal to 10 percent, 2 is assigned if the CSR/AHI burden is increasing and between 10 and 20 percent, and a score of 3 is assigned if the CSR/AHI burden is increasing and greater than 20 percent.

By way of example, assume that the sensors indicate that the patient's heart rate is 58 bpm, there is no detectable A-V block, MAP is 63 mmHg, PE status decreases 18 percent, respiration rate is 20 br/min, and there is no change in CSR/AHI burden. Under these circumstances, the patient would be assigned a score of 1 for heart rate, 0 for A-V block, 2 for MAP, 2 for ITTI, 0 for dyspnea, and 0 for CSR/AHI burden.

After the score is assigned to each sensor parameter, the individual scores are summed to form a net composite index score. In the example in the paragraph above, the patient's net composite index score would be 1+0+2+2+0+0=5.

At step 60, the controller evaluates the net composite index score and recommends an appropriate level of monitoring. Based on the composite index score, at step 62 the controller may transmit a warning signal to a medical professional or the patient or both that is associated with a recommended course of action. For example, the net composite index score may be used as an input to a titration response matrix. An example titration response matrix is shown below:

| Composite index | Device Action | Recommended Action |
| --- | --- | --- |
| 0 to 2 points | Monitoring | No action required |
| 3 to 6 points | Yellow sign | More attention required |
| 7 to 12 points | Orange sign | Close attention required |
| >12 points | Red sign | Immediate attention required |

Other embodiments of a titration response matrix are usable. Of course, in various embodiments where various numbers or combinations of sensors are present, the composite index will be adjusted accordingly. For example, where fewer sensors are present, it is expected that the composite index thresholds will be lower, or where greater numbers of sensors are present, the composite index thresholds will be higher. As mentioned above, in some embodiments, the score threshold values for each response are programmable by a user. The desired response for any particular net composite index score may be programmable by medical personnel such as a physician. In the response matrix above, if the net composite index score is 0 to 2, then the controller does not recommend that any cautionary action be taken. Generally, under this condition, a physician should feel free to up-titrate the drug dosage at the pre-defined titration interval if the maximum dosage is not exceeded and the desired beneficial effects of the drug have not been attained. The beneficial effects of the drug may be determined according to the judgment or perceptions of a physician or other medical profession, and this may be based in part or in whole on data collected by an implantable medical device.

As also shown in the response matrix above, if the net composite index score is 3 to 6, then the controller generates a "yellow flag" warning, which can be communicated to medical personnel either through direct telemetry to a programmer module in a medical facility, or through telemetry to a programmer that is near the patient (such as in the patient's home) and that is configured to communicate with a computer in a medical facility, such as through a telephone connection. When a "yellow flag" warning is generated, the physician or other medical professional responsible for the care of the patient should be aware that the patient is exhibiting signs that the drug is producing measurable side effects and should closely monitor the patient and take this into account before increasing the dosage of the drug.

If the patient has a net composite index score of 7 to 12, then the controller generates an "orange flag" warning that can be communicated to the medical professionals responsible for the patient's care. This "orange flag" warning should place the medical professionals on a state of heightened alert because the side effects of the drug are having distinct negative consequences for the patient. Most likely, under these conditions the patient's dosage should not be increased, or possibly should be decreased. If the patient's net composite index score is greater than 12, the controller generates a "red flag" warning. In one embodiment, if this occurs outside of a medical facility, the controller may be configured to provide an immediate warning to the patient. This may include an audible signal that the patient has been taught to recognize as a warning signal, or it may include transmitting a signal to a programmer that is in the patient's home or other location that can display a message that the patient can perceive and understand. The warning generated by the controller under these conditions may be associated with a need to receive prompt or immediate medical attention. Most likely under these circumstances the patient's dosage should be decreased until the side effects moderate. In various embodiments, various other responses are configured, such as providing for different actions to be taken in response to a range of composite index scores or using different composite index limits to define a particular action to be taken.

In some embodiments, if any individual score is at a certain high or maximum value, such as any parameter that is assigned a score of "3" in the matrix above, the controller may be configured to recommend at step 64 that the patient's dosage be held constant or decreased. In some further embodiments, the controller may be configured to transmit a warning to the patient and medical personnel at step 62 if any parameter is assigned a high or maximum value. A warning transmitted at step 62 is generally configured to notify the appropriate personnel, potentially including the patient and the patient's medical care providers, of the need for prompt treatment.

At step 64, the controller provides an indication to a physician or other medical personnel regarding a recommended drug dosage for the patient that is based on the composite index. For example, where the composite index indicates that the patient's side effects are insignificant, then the controller will indicate that the patient's drug dosage can be or should be increased at the next scheduled titration event. This indication may also be based in part on whether the desired beneficial effect of the drug has been achieved and whether the patient is at the maximum recommended dosage. However, although the controller may make a recommendation based on the composite index, ultimately the beneficial effect of the drug is evaluated by the physician or other medical person, based on measurements and subjective symptomatic perceptions of the patient. The indication that the patient's dosage can be increased is generally only made if the patient's net composite index score indicates that the side effects of the drug are insignificant, or at least are not serious. This indication can be communicated to the physician, such as through telemetry or through a telephone network or other communication network.

After the controller provides an indication at step 64, the controller is usually configured to repeat the cycle, returning to step 54 to monitor the amount of time since the last titration, and then to step 56 of receiving sensor data, and so forth. The controller may be configured to repeat the steps of algorithm 50 either continuously, at regular time intervals, or only at a certain time or time window after the patient's dosage has been increased. It is possible that the controller will provide an indication at step 64 that the dosage can be increased, but before the dosage is actually increased, that the patient's side effects change to the point that a warning signal is transmitted at step 62. Once a warning signal is transmitted at step 62, the controller may continue to monitor the patient's side effects to determine if they worsen, but generally the controller will be configured to not provide an indication that the dosage can be increased once the controller has detected side effects sufficient to generate a warning. However, various embodiments may be configured to treat this situation in a different manner, and the controller's response may be a configurable parameter.

In one embodiment, the various index values can be combined through a formula that weights each factor individually. By way of example, the patient's resting heart rate could be given greater weight than the patient's CSR/AHI burden. In this case, the composite index may need to be adjusted to account for this weighting factor. In one embodiment, a relatively small change in heart rate may have a greater effect on determining the recommended course of action (including whether the drug dosage should be increased) than another parameter, such as CSR/AHI burden.

In one embodiment, the measurements of side effects are only made when the patient is at rest. To determine whether the patient is at rest, the drug titration system 20 may further include an accelerometer for monitoring the patient's physical activity and posture. For example, the accelerometer may be a 3-axis accelerometer that can detect the patient's posture with respect to the earth's gravitational field, such as by determining whether the patient is lying in a horizontal position or standing in a vertical position. Furthermore, the accelerometer may determine whether the patient is generally physically at rest, or whether the patient is generally physically active. In one embodiment, the various other sensors are used to determine whether the patient is at rest, such as by evaluating the patient's respiration rate. Generally, the drug titration system may be configured to wait to take any measurements of side effects until the patient is in a resting state. The range of sensor values that correspond to a resting state may be a programmable value that can be changed by a physician or other medical professional.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

The above specification provides a complete description of the structure and use of the invention. Since many of the embodiments of the invention can be made without parting from the spirit and scope of the invention, the invention resides in the claims.

What is claimed is:

1. A method comprising:
   (i) providing an implantable medical device having a controller;
   (ii) providing one or more implantable sensors configured to sense physical parameters of the patient and configured to transmit signals to the controller;
   (iii) receiving signals from the one or more sensors at the controller;
   (iv) processing the received signals to determine at least two cardiopulmonary characteristics of the patient;
   (v) determining a composite index based on the at least two cardiopulmonary characteristics; and
   (vi) generating a signal based on the composite index by a controller, where the signal provides an indication of the effectiveness of a beta-blocker or side effects of the beta blocker.

2. The method of claim 1, further comprising the step of assigning an index value to each cardiopulmonary characteristic based on its nature or degree.

3. The method of claim 1, where the implantable sensor is a blood pressure sensor.

4. The method of claim 1, where the implantable sensor is a respiration sensor.

5. The method of claim 4, where the respiration sensor is an intra-thoracic impedance sensor.

6. The method of claim 1, where the implantable sensor is an electrocardiogram sensor that receives cardiac electrical signals.

7. The method of claim 1, where processing the signals includes determining a heart rate from a cardiac electrical signal.

8. The method of claim 1, where processing the signals includes determining the presence and degree of arrhythmias.

9. The method of claim 1, where processing the signals includes determining mean arterial pressure.

10. The method of claim 1, where processing the signals includes determining pulmonary edema status.

11. The method of claim 1, where processing the signals includes determining the presence and degree of dyspnea.

12. The method of claim 1, where processing the signals includes determining CSR/AHI burden.

13. The method of claim 1, further comprising providing a non-implantable sensor that is configured to transmit signals.

14. The method of claim 1, where the one or more implantable sensors comprises a sensor for determining a patient's posture and activity level, and where the step of determining a composite index occurs only when the sensor indicates that the patient is in a pre-selected state.

15. The method of claim 14, where the pre-selected state corresponds to the patient being at rest and supine.

16. The method of claim 1, further comprising the step of determining if a scheduled titration event timing has been exceeded, and if so, generating a signal that is indicative of the fact that the schedule titration event timing has been exceeded.

17. The method of claim 1, where the step of processing the received signals to determine at least two cardiopulmonary characteristics of the patient occurs in the controller.

18. The method of claim 1, further comprising the step of providing a second, non-implantable controller.

19. The method of claim 18, where the step of processing the received signals to determine at least two cardiopulmonary characteristics of the patient occurs in the second, non-implantable controller.

20. A medical device system for use with a drug titration protocol, the medical device system comprising:
   (i) an implantable controller;
   (ii) one or more implantable sensors configured to sense physical parameters of the patient and configured to transmit signals to the controller; and
   (iii) wherein the system is configured to
      (a) receive signals from the one or more sensors and process the received signals to determine at least two cardiopulmonary characteristics of the patient;
      (b) determine a composite index based on the at least two cardiopulmonary characteristics; and
      (c) generate a signal based on the composite index, where the signal provides an indication of the effectiveness of a beta-blocker or side effects of the beta blocker.

21. The medical device system of claim 20, wherein the system is further configured to assign an index value to each cardiopulmonary characteristic based on its nature or degree.

22. The medical device system of claim 20, where processing a signal includes determining the presence and degree of arrhythmia.

23. The medical device system of claim 20, where processing a signal includes determining mean arterial pressure.

24. The medical device system of claim 20, where processing a signal includes determining pulmonary edema status.

25. The medical device system of claim 20, where processing a signal includes determining the presence and degree of dyspnea.

26. The medical device system of claim 20, where processing a signal includes determining Cheyne-Stokes Respiration/Apnea Hypopnea Index burden.

27. The medical device system of claim 20, where the implantable sensor is an electrocardiogram sensor that receives cardiac electrical signals.

28. The medical device system of claim 27, where processing a signal includes determining a resting heart rate from a cardiac electrical signal.

29. A medical device system for use with a drug titration protocol, the medical device system comprising:
   (i) an implantable controller;
   (ii) a plurality of implantable sensors configured to sense physical parameters of the patient and configured to transmit signals to the controller, the plurality of implantable sensors including at least:
- (a) an electrocardiogram sensor that receives cardiac electrical signals;
- (b) a blood pressure sensor; and
- (c) an intra-thoracic impedance sensor; and (iii) wherein the controller is configured to
- (a) receive signals from the plurality of sensors and process the received signals to determine associated physical characteristics of the patient, including determining:
  - (A) heart rate;
  - (B) mean arterial blood pressure;
  - (C) the presence and degree of atrio-ventricular block;
  - (D) pulmonary edema status;
  - (E) the presence and degree of dyspnea; and
  - (F) CSR/AHI burden;
- (b) assign an index value to each physical characteristic based on its nature or degree;
- (c) determine a composite index of physical characteristics by combining the individual index values; and
- (d) generate a signal based on the composite index, where the signal provides an indication of side effects of a beta-blocker or the effectiveness of a beta-blocker.

* * * * *